United States Patent [19]

Bundy

[11] 4,166,912

[45] Sep. 4, 1979

[54] 9-DEOXY-9-METHYLENE-INTER-PHENYLENE-16-PHENYL-PGF COMPOUNDS

[75] Inventor: Gordon L. Bundy, Portage, Mich.

[73] Assignee: The Upjohn Company, Kalamazoo, Mich.

[21] Appl. No.: 924,035

[22] Filed: Jul. 12, 1978

Related U.S. Application Data

[63] Continuation-in-part of Ser. No. 786,249, Apr. 11, 1977, Pat. No. 4,118,584.

[51] Int. Cl.$^2$ .......................................... C07C 177/00
[52] U.S. Cl. ........................................ 560/61; 560/62; 560/63; 560/55; 260/343; 562/465; 562/471; 562/472

[58] Field of Search ..................... 560/61, 62, 63, 55; 260/343; 562/465, 471, 472

[56] References Cited

PUBLICATIONS

Derwent Abstract, 79369Y/45, BE 854-271, 04-11-77.

*Primary Examiner*—Paul J. Killos
*Attorney, Agent, or Firm*—Robert A. Armitage

[57] ABSTRACT

The present invention relates to novel 9-deoxy-9-methylene-inter-phenylene-16-phenyl-PGF compounds.

These compounds are useful pharmacological agents, and are useful for the same purposes as the corresponding PGE-type compounds.

127 Claims, No Drawings

9-DEOXY-9-METHYLENE-INTER-PHENYLENE-16-PHENYL-PGF COMPOUNDS

CROSS REFERENCE TO RELATED APPLICATIONS

This application is a continuation-in-part of Ser. No. 786,249, filed Apr. 11, 1977, now issued as U.S. Pat. No. 4,118,584.

The present invention relates to novel 9-deoxy-9-methylene-inter-phenylene-16-phenyl-PGF compounds, the essential material constituting a disclosure of which is incorporated here by reference from U.S. Pat. No. 4,118,584.

I claim:

1. A prostaglandin analog of the formula

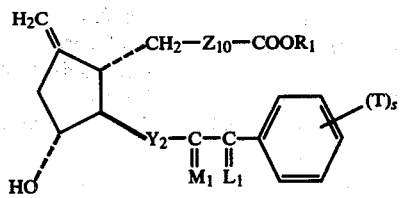

wherein $Y_2$ is trans—CH=CH— or —CH$_2$CH$_2$—;
wherein $M_1$ is

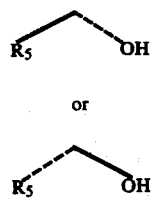

or wherein $R_5$ is hydrogen or methyl;
wherein $L_1$ is

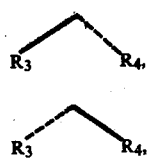

or a mixture of

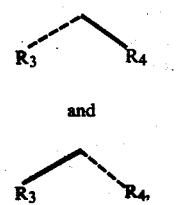

and wherein $R_3$ and $R_4$ are hydrogen, methyl, or fluoro, being the same or different, with the proviso that one of $R_3$ and $R_4$ is fluoro only when the other is hydrogen or fluoro;
wherein $Z_{10}$ is

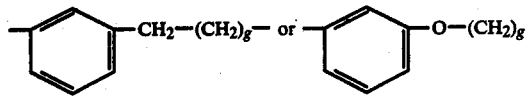

wherein g is one, 2, or 3;
wherein T is chloro, fluoro, trifluoromethyl, alkyl of one to 3 carbon atoms, inclusive, or alkoxy of one to 3 carbon atoms, inclusive, and s is zero, one, 2, or 3, the various T's being the same or different, with the proviso that not more than two T's are other than alkyl;
wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, two, or three chloro or alkyl of one to 3 carbon atoms, inclusive, or a pharmacologically acceptable cation, and the 1,11- or 1,15-lactones thereof.

2. A prostaglandin analog according to claim 1, wherein $Y_2$ is —CH$_2$CH$_2$—.

3. A prostaglandin analog according to claim 2, wherein $Z_{10}$ is

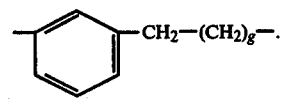

4. A prostaglandin analog according to claim 3, wherein $M_1$ is

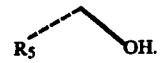

5. 9-Deoxy-9-methylene-15-epi-3,7-inter-m-phenylene-4,5,6,17,18,19,20-heptanor-16-phenyl-13,14-dihydro-PGF$_1$, a prostaglandin analog according to claim 4.

6. A prostaglandin analog according to claim 3, wherein $M_1$ is

7. A prostaglandin analog according to claim 6, wherein s is zero, or one and T is chloro, fluoro, or trifluoromethyl.

8. A prostaglandin analog according to claim 7, wherein g is 3.

9. 9-Deoxy-9-methylene-2a,2b-dihomo-15-methyl-3,7-inter-m-phenylene-4,5,6,17,18,19,20-heptanor-16-phenyl-13,14-didehydro-PGF$_1$, a prostaglandin analog according to claim 8.

10. 9-Deoxy-9-methylene-2a,2b-dihomo-3,7-inter-m-phenylene-4,5,6,17,18,19,20-heptanor-16-phenyl-13,14-dihydro-PGF$_1$, a prostaglandin analog according to claim 8.

11. A prostaglandin analog according to claim 7, wherein g is 1.

12. A prostaglandin analog according to claim 11, wherein at least one of $R_3$ and $R_4$ is methyl.

13. A prostaglandin analog according to claim 12, wherein $R_3$ and $R_4$ are both methyl.

14. 9-Deoxy-9-methylene-16-methyl-3,7-inter-m-phenylene-4,5,6,18,19,20-hexanor-16-phenyl-13,14-dihydro-PGF₁, a prostaglandin analog according to claim 13.

15. A prostaglandin analog according to claim 11, wherein at least one of R₃ and R₄ is fluoro.

16. A prostaglandin analog according to claim 15, wherein R₃ and R₄ are both fluoro.

17. 9-Deoxy-9-methylene-16,16-difluoro-3,7-inter-m-phenylene-4,5,6,17,18,19,20-heptanor-16-phenyl-13,14-dihydro-PGF₁, a prostaglandin analog according to claim 16.

18. A prostaglandin analog according to claim 11, wherein R₃ and R₄ are both hydrogen.

19. A prostaglandin analog according to claim 18, wherein R₅ is methyl.

20. 9-Deoxy-9-methylene-15-methyl-3,7-inter-m-phenylene-4,5,6,17,18,19,20-heptanor-16-phenyl-13,14-dihydro-PGF₁, a prostaglandin analog according to claim 19.

21. A prostaglandin analog according to claim 18, wherein R₅ is hydrogen.

22. 9-Deoxy-9-methylene-3,7-inter-m-phenylene-4,5,6,17,18,19,20-heptanor-16-phenyl-13,14-dihydro-PGF₁, a prostaglandin analog according to claim 21.

23. A prostaglandin analog according to claim 2, wherein $Z_{10}$ is

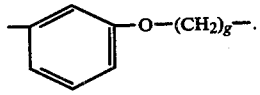

24. A prostaglandin analog according to claim 2, wherein $M_1$ is

25. A prostaglandin analog according to claim 24, wherein s is zero or one and T is chloro, fluoro, or trifluoromethyl.

26. A prostaglandin analog according to claim 25, wherein g is 3.

27. 9-Deoxy-9-methylene-2a,2b-dihomo-15-epi-15-methyl-16-phenyl-3,7-inter-m-phenylene-4,5,6,17,18,19,20-heptanor-13,14-dihydro-3-oxa-PGF₁, a prostaglandin analog according to claim 26.

28. 9-Deoxy-9-methylene-2a,2b-dihomo-15-epi-16-phenyl-3,7-inter-m-phenylene-4,5,6,17,18,19,20-heptanor-13,14-dihydro-3-oxa-PGF₁, a prostaglandin analog according to claim 26.

29. A prostaglandin analog according to claim 25, wherein g is 1.

30. A prostaglandin analaog according to claim 29, wherein at least one of R₃ and R₄ is methyl.

31. 9-Deoxy-9-methylene-15-epi-16-methyl-16-phenyl-3,7-inter-m-phenylene-4,5,6,18,19,20-hexanor-13,14-dihydro-3-oxa-PGF₁, a prostaglandin analog according to claim 30.

32. A prostaglandin analog according to claim 29, wherein at least one of R₃ and R₄ is fluoro.

33. 9-Deoxy-9-methylene-15-epi-16,16-difluoro-16-phenyl-3,7-inter-m-phenylene-4,5,6,17,18,19,20-heptanor-13,14-dihydro-3-oxa-PGF₁, a prostaglandin analog according to claim 32.

34. A prostaglandin analog according to claim 29, wherein R₃ and R₄ are both hydrogen.

35. 9-Deoxy-9-methylene-15-epi-16-methyl-16-phenyl-3,7-inter-m-phenylene-4,5,6,17,18,19,20-heptanor-13,14-dihydro-3-oxa-PGF₁, a prostaglandin analog according to claim 34.

36. A prostaglandin analog according to claim 23, wherein $M_1$ is

37. A prostaglandin analog according to claim 36, wherein s is zero or one and T is chloro, fluoro, or trifluoromethyl.

38. A prostaglandin analog according to claim 37, wherein g is 3.

39. A prostaglandin analog according to claim 38, wherein at least one of R₃ and R₄ is methyl.

40. 9-Deoxy-9-methylene-2a,3b-dihomo-16-methyl-16-phenyl-3,7-inter-m-phenylene-4,5,6,18,19,20-hexanor-13,14-dihydro-3-oxa-PGF₁, a prostaglandin analog according to claim 39.

41. A prostaglandin analog according to claim 38, wherein at least one of R₃ and R₄ is fluoro.

42. 9-Deoxy-9-methylene-2a,3b-dihomo-16,16-difluoro-16-phenyl-3,7-inter-m-phenylene-4,5,6,17,18,19,20-heptanor-13,14-dihydro-3-oxa-PGF₁, a prostaglandin analog according to claim 41.

43. A prostaglandin analog according to claim 38, wherein R₃ and R₄ are both hydrogen.

44. 9-Deoxy-9-methylene-2a,2b-dihomo-16-phenyl-3,7-inter-m-phenylene-4,5,6,17,18,19,20-heptanor-13,14-dihydro-3-oxa-PGF₁, a prostaglandin analog according to claim 43.

45. A prostaglandin analog according to claim 27, wherein g is 1.

46. A prostaglandin analog according to claim 45, wherein at least one of R₃ and R₄ is methyl.

47. A prostaglandin analog according to claim 46, wherein R₃ and R₄ are both methyl.

48. 9-Deoxy-9-methylene-16-methyl-16-phenyl-3,7-inter-m-phenylene-4,5,6,18,19,20-hexanor-13,14-dihydro-3-oxa-PGF₁, tris-(hydroxymethyl)-aminomethane salt, a prostaglandin analog according to claim 47.

49. 9-Deoxy-9-methylene-16-methyl-16-phenyl-3,7-inter-m-phenylene-4,5,6,18,19,20-hexanor-13,14-dihydro-3-oxa-PGF₁, methyl ester, a prostaglandin analog according to claim 47.

50. 9-Deoxy-9-methylene-16-methyl-16-phenyl-3,7-inter-m-phenylene-4,5,6,18,19,20-hexanor-13,14-dihydro-3-oxa-PGF₁, methyl ester, a prostaglandin analog according to claim 47.

51. A prostaglandin analog according to claim 45, wherein at least one of R₃ and R₄ is fluoro.

52. A prostaglandin analog according to claim 51, wherein R₃ and R₄ are both fluoro.

53. A prostaglandin analog according to claim 52, wherein R₅ is methyl.

54. 9-Deoxy-9-methylene-15-methyl-16,16-difluoro-16-phenyl-3,7-inter-m-phenylene-4,5,6,17,18,19,20-heptanor-13,14-dihydro-3-oxa-PGF₁, a prostaglandin analog according to claim 53.

55. A prostaglandin analog according to claim 52, wherein R₅ is hydrogen.

56. 9-Deoxy-9-methylene-16,16-difluoro-16-phenyl-3,7-inter-m-phenylene-4,5,6,17,18,19,20-heptanor-13,14-dihydro-3-oxa-PGF₁, a prostaglandin analog according to claim 55.

57. A prostaglandin analog according to claim 45, wherein $R_3$ and $R_4$ are both hydrogen.

58. A prostaglandin analog according to claim 57, wherein $R_5$ is methyl.

59. 9-Deoxy-9-methylene-15-methyl-16-phenyl-3,7-inter-m-phenylene-4,5,6,17,18,19,20-heptanor-13,14-dihydro-3-oxa-PGF$_1$, tris(hydroxymethyl)aminomethane salt, a prostaglandin analog according to claim 58.

60. 9-Deoxy-9-methylene-15-methyl-16-phenyl-3,7-inter-m-phenylene-4,5,6,17,18,19,20-heptanor-13,14-dihydro-3-oxa-PGF$_1$, methyl ester, a prostaglandin analog according to claim 58.

61. 9-Deoxy-9-methylene-15-methyl-16-phenyl-3,7-inter-m-phenylene-4,5,6,17,18,19,20-heptanor-13,14-dihydro-3-oxa-PGF$_1$, a prostaglandin analog according to claim 58.

62. A prostaglandin analog according to claim 57, wherein $R_5$ is hydrogen.

63. 9-Deoxy-9-methylene-16-phenyl-3,7-inter-m-phenylene-4,5,6,17,18,19,20-heptanor-13,14-dihydro-3-oxa-PGF$_1$, methyl ester, a prostaglandin analog according to claim 62.

64. 9-Deoxy-9-methylene-16-phenyl-3,7-inter-m-phenylene-4,5,6,17,18,19,20-heptanor-13,14-dihydro-3-oxa-PGF$_1$, a prostaglandin analog according to claim 62.

65. A prostaglandin analog according to claim 1, wherein $Y_2$ is trans—CH=CH—.

66. A prostaglandin analog according to claim 65, wherein $Z_{10}$ is

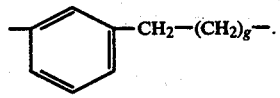

67. A prostaglandin analog according to claim 66, wherein $M_1$ is

68. 9-Deoxy-9-methylene-15-epi-3,7-inter-m-phenylene-4,5,6,17,18,19,20-heptanor-16-phenyl-PGF$_1$, a prostaglandin analog according to claim 67.

69. A prostaglandin analog according to claim 66, wherein $M_1$ is

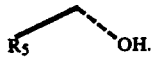

70. A prostaglandin analog according to claim 69, wherein s is zero or one and T is chloro, fluoro, or trifluoromethyl.

71. A prostaglandin analog according to claim 70, wherein g is 3.

72. 9-Deoxy-9-methylene-2a,2b-dihomo-15-methyl-3,7-inter-m-phenylene-4,5,6,17,18,19,20-heptanor-16-phenyl-PGF$_1$, a prostaglandin analog according to claim 71.

73. 9-Deoxy-9-methylene-2a,2b-dihomo-3,7-inter-m-phenylene-4,5,6,17,18,19,20-heptanor-16-phenyl-PGF$_1$, a prostaglandin analog according to claim 71.

74. A prostaglandin analog according to claim 70, wherein g is 1.

75. A prostaglandin analog according to claim 74, wherein at least one of $R_3$ and $R_4$ is methyl.

76. A prostaglandin analog according to claim 75, wherein $R_3$ and $R_4$ are both methyl.

77. 9-Deoxy-9-methylene-16-methyl-3,7-inter-m-phenylene-4,5,6,18,19,20-hexanor-16-phenyl-PGF$_1$, a prostaglandin analog according to claim 76.

78. A prostaglandin analog according to claim 74, wherein at least one of $R_3$ and $R_4$ is fluoro.

79. A prostaglandin analog according to claim 78, wherein $R_3$ and $R_4$ are both fluoro.

80. 9-Deoxy-9-methylene-16,16-difluoro-3,7-inter-m-phenylene-4,5,6,17,18,19,20-heptanor-16-phenyl-PGF$_1$, a prostaglandin analog according to claim 79.

81. A prostaglandin analog according to claim 74, wherein $R_3$ and $R_4$ are both hydrogen.

82. A prostaglandin analog according to claim 81, wherein $R_5$ is methyl.

83. 9-Deoxy-9-methylene-15-methyl-3,7-inter-m-phenylene-4,5,6,17,18,19,20-heptanor-16-phenyl-PGF$_1$, a prostaglandin analog according to claim 82.

84. A prostaglandin analog according to claim 81, wherein $R_5$ is hydrogen.

85. 9-Deoxy-9-methylene-3,7-inter-m-phenylene-4,5,6,17,18,19,20-heptanor-16-phenyl-PGF$_1$, a prostaglandin analog according to claim 84.

86. A prostaglandin analog according to claim 65, wherein $Z_{10}$ is

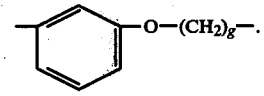

87. A prostaglandin analog according to claim 86, wherein $M_1$ is

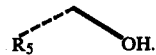

88. A prostaglandin analog according to claim 87, wherein s is zero or one and T is chloro, fluoro, or trifluoromethyl.

89. A prostaglandin analog according to claim 88, wherein g is 3.

90. 9-Deoxy-9-methylene-2a,2b-dihomo-15-epi-15-methyl-16-phenyl-3,7-inter-m-phenylene-4,5,6,17,18,19,20-heptanor-3-oxa-PGF$_1$, a prostaglandin analog according to claim 89.

91. 9-Deoxy-9-methylene-2a,2b-dihomo-15-epi-16-phenyl-3,7-inter-m-phenylene-4,5,6,17,18,19,20-heptanor-3-oxa-PGF$_1$, a prostaglandin analog according to claim 89.

92. A prostaglandin analog according to claim 88, wherein g is 1.

93. A prostaglandin analog according to claim 92, wherein at least one of $R_3$ and $R_4$ is methyl.

94. 9-Deoxy-9-methylene-15-epi-16-methyl-16-phenyl-3,7-inter-m-phenylene-4,5,6,18,19,20-hexanor-3-oxa-PGF$_1$, a prostaglandin analog according to claim 89.

95. A prostaglandin analog according to claim 92, wherein at least one of $R_3$ and $R_4$ is fluoro.

96. 9-Deoxy-9-methylene-15-epi-16,16-difluoro-16-phenyl-3,7-inter-m-phenylene-4,5,6,17,18,19,20-heptanor-3-oxa-PGF$_1$, a prostaglandin analog according to claim 95.

97. A prostaglandin analog according to claim 92, wherein $R_3$ and $R_4$ are both hydrogen.

98. 9-Deoxy-9-methylene-15-epi-15-methyl-16-phenyl-3,7-inter-m-phenylene-4,5,6,17,18,19,20-heptanor-3-oxa-PGF$_1$, a prostaglandin analog according to claim 97.

99. A prostaglandin analog according to claim 86, wherein M$_1$ is

100. A prostaglandin analog according to claim 99, wherein s is zero or one and T is chloro, fluoro, or trifluoromethyl.

101. A prostaglandin analog according to claim 100, wherein g is 3.

102. A prostaglandin analog according to claim 101, wherein at least one of R$_3$ and R$_4$ is methyl.

103. 9-Deoxy-9-methylene-2a,2b-dihomo-16-methyl-16-phenyl-3,7-inter-m-phenylene-4,5,6,18,19,20-hexanor-3-oxa-PGF$_1$, a prostaglandin analog according to claim 102.

104. A prostaglandin analog according to claim 101, wherein at least one of R$_3$ and R$_4$ is fluoro.

105. 9-Deoxy-9-methylene-2a,2b-dihomo-16,16-difluoro-16-phenyl-3,7-inter-m-phenylene-4,5,6,17,18,19,20-heptanor-3-oxa-PGF$_1$, a prostaglandin analog according to claim 102.

106. A prostaglandin analog according to claim 101, wherein R$_3$ and R$_4$ are both hydrogen.

107. 9-Deoxy-9-methylene-2a,2b-dihomo-15-methyl-16-phenyl-3,7-inter-m-phenylene-4,5,6,17,18,19,20-heptanor-3-oxa-PGF$_1$, a prostaglandin analog according to claim 106.

108. A prostaglandin analog according to claim 100, wherein g is 1.

109. A prostaglandin analog according to claim 108, wherein at least one of R$_3$ and R$_4$ is methyl.

110. A prostaglandin analog according to claim 109, wherein R$_3$ and R$_4$ are both methyl.

111. 9-Deoxy-9-methylene-16-methyl-16-phenyl-3,7-inter-m-phenylene-4,5,6,18,19,20-hexanor-3-oxa-PGF$_1$, tris(hydroxymethyl)aminoethane salt, a prostaglandin analog according to claim 110.

112. 9-Deoxy-9-methylene-16-methyl-16-phenyl-3,7-inter-m-phenylene-4,5,6,18,19,20-hexanor-3-oxa-PGF$_1$, methyl ester, a prostaglandin analog according to claim 110.

113. 9-Deoxy-9-methylene-16-methyl-16-phenyl-3,7-inter-m-phenylene-4,5,6,18,19,20-hexanor-3-oxa-PGF$_1$, a prostaglandin analog according to claim 110.

114. A prostaglandin analog according to claim 108, wherein at least one of R$_3$ and R$_4$ is fluoro.

115. A prostaglandin analog according to claim 114, wherein R$_3$ and R$_4$ are both fluoro.

116. A prostaglandin analog according to claim 115, wherein R$_5$ is methyl.

117. 9-Deoxy-9-methylene-15-methyl-16,16-difluoro-16-phenyl-3,7-inter-m-phenylene-4,5,6,17,18,19,20-heptanor-3-oxa-PGF$_1$, a prostaglandin analog according to claim 116.

118. A prostaglandin analog according to claim 115, wherein R$_5$ is hydrogen.

119. 9-Deoxy-9-methylene-16,16-difluoro-16-phenyl-3,7-inter-m-phenylene-4,5,6,17,18,19,20-heptanor-3-oxa-PGF$_1$, a prostaglandin analog according to claim 118.

120. A prostaglandin analog according to claim 118, wherein R$_3$ and R$_4$ are both hydrogen.

121. A prostaglandin analog according to claim 120, wherein R$_5$ is methyl.

122. 9-Deoxy-9-methylene-15-methyl-16-phenyl-3,7-inter-m-phenylene-4,5,6,17,18,19,20-heptanor-3-oxa-PGF$_1$, tris(hydroxymethyl)aminomethane salt, a prostaglandin analog according to claim 121.

123. 9-Deoxy-9-methylene-15-methyl-16-phenyl-3,7-inter-m-phenylene-4,5,6,17,18,19,20-heptanor-3-oxa-PGF$_1$, methyl ester, a prostaglandin analog according to claim 121.

124. 9-Deoxy-9-methylene-15-methyl-16-phenyl-3,7-inter-m-phenylene-4,5,6,17,18,19,20-heptanor-3-oxa-PGF$_1$, a prostaglandin analog according to claim 121.

125. A prostaglandin analog according to claim 120, wherein R$_5$ is hydrogen.

126. 9-Deoxy-9-methylene-16-phenyl-3,7-inter-m-phenylene-4,5,6,17,18,19,20-heptanor-3-oxa-PGF$_{11}$, methyl ester, a prostaglandin analog according to claim 125.

127. 9-Deoxy-9-methylene-16-phenyl-3,7-inter-m-phenylene-4,5,6,17,18,19,20-heptanor-3-oxa-PGF$_1$, a prostaglandin analog according to claim 125.

* * * * *

UNITED STATES PATENT OFFICE
CERTIFICATE OF CORRECTION

Patent No.  4,166,912    Dated  4 September 1979

Inventor(s)  Gordon L. Bundy

It is certified that error appears in the above-identified patent and that said Letters Patent are hereby corrected as shown below:

Column 2, line 55, "13,14-didehydro-" should read -- 13,14-dihydro- --;

Column 3, line 32, "according to claim 2" should read -- according to claim 23 --; line 67, "16-methyl-" should read -- 15-methyl- --;

Column 4, line 17 and line 24, "2a,3b-dihomo-" should read -- 2a,2b-dihomo- --; line 50, "PGF$_1$, methyl ester" should read -- PGF$_1$, --.

Signed and Sealed this

Fourteenth Day of October 1980

[SEAL]

Attest:

Attesting Officer

SIDNEY A. DIAMOND

Commissioner of Patents and Trademarks